United States Patent [19]
Rao

[11] Patent Number: 6,015,941
[45] Date of Patent: Jan. 18, 2000

[54] PEPTIDE DERIVATIVES OF TACHYPLESIN HAVING ANTIMICROBIAL ACTIVITY

[75] Inventor: A. Gururaj Rao, Urbandale, Iowa

[73] Assignee: Pioneer Hi-Bred International, Inc., Des Moines, Iowa

[21] Appl. No.: 08/962,034

[22] Filed: Oct. 31, 1997

[51] Int. Cl.[7] .............. C12N 15/29; C12N 5/04; A01H 5/00; A01H 4/00
[52] U.S. Cl. .............. 800/279; 514/2; 424/405; 536/32.6; 536/23.1; 800/298; 800/278; 800/295; 435/69.1; 435/70.1; 435/468; 435/410; 435/418; 435/419
[58] Field of Search .............. 514/2; 47/58; 424/405; 800/298, 278, 279, 295; 435/69.1, 70.1, 468, 410, 418, 419; 536/23.1, 23.6, 23.7

[56] References Cited

U.S. PATENT DOCUMENTS 5,589,624 12/1996 Ulbrich et al. .............. 800/205

FOREIGN PATENT DOCUMENTS

| | | | |
|---|---|---|---|
| 545730 | 6/1993 | European Pat. Off. | |
| WO 9516776 | 6/1995 | WIPO . | |
| WO 96/37508 | 11/1996 | WIPO .............. | C07K 7/08 |
| WO 97/02287 | 1/1997 | WIPO .............. | C07K 7/06 |

OTHER PUBLICATIONS

Linthorst et al. Plant Cell. 1989. vol. 1: 285–291.
Liu et al. Proc. Natl. Acad. Sci. 1994. vol. 91: 1888–1892.
Zhong et al. 1995 Int. J. Pept. protein. Res. vol. 45: 337–347.
A. Gururaj Rao, (1995) *Design and synthesis of amphipathic antimicrobial peptides*, 45:337–347; Sep. 12, 1994.
R. J. Putnam and A.G. Rao (1994) *Structure–funtion studies on the antimicrobial activity of tachyplesin through the synthesis of linear analogs.*
A. Gururaj Rao, et al. (1992) *Int. J. Peptide Protein Res.* 40:507–514.
A. Gururaj Rao (1995) *Antimicrobial Peptides* MPMI vol. 8, No. 1, pp. 6–13.

*Primary Examiner*—Lynette R. F. Smith
*Assistant Examiner*—Ousama M-Faiz Zaghmout
*Attorney, Agent, or Firm*—Alston & Bird LLP

[57] ABSTRACT

Compositions comprising antimicrobial peptides are provided. The peptides are derivatives of tachyplesin having amino acid substitutions in which the four cysteine residues are replaced with hydrophobic amino acids. The compositions are useful in methods of the control of fungal and bacterial activity in agricultural and medical applications. Methods for making and using the compounds of the invention are additionally provided.

24 Claims, 4 Drawing Sheets

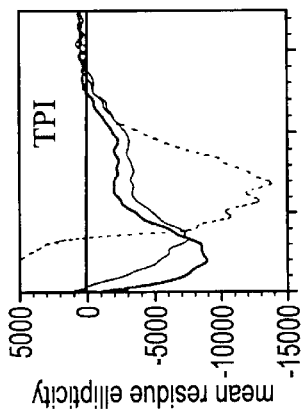
Fig. 1G TPI
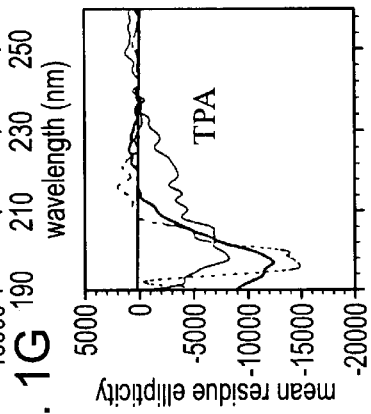
Fig. 1H TPA
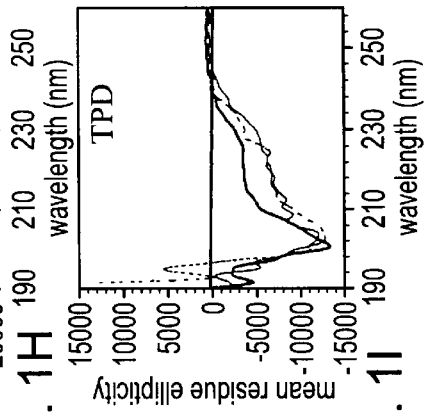
Fig. 1I TPD
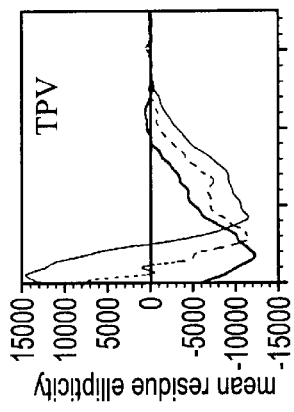
Fig. 1D TPV
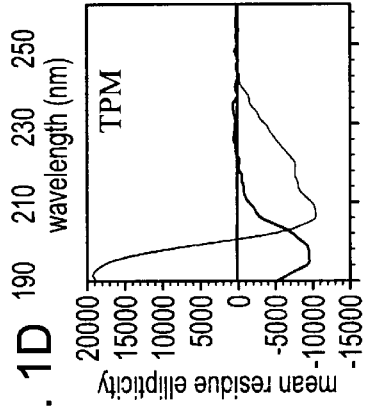
Fig. 1E TPM
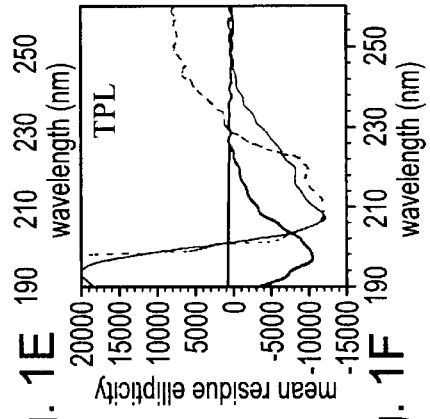
Fig. 1F TPL
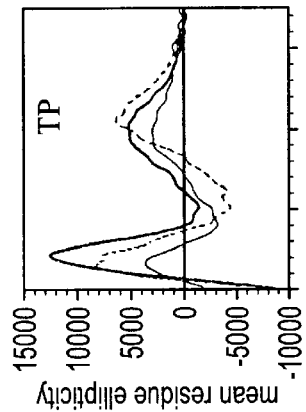
Fig. 1A TP
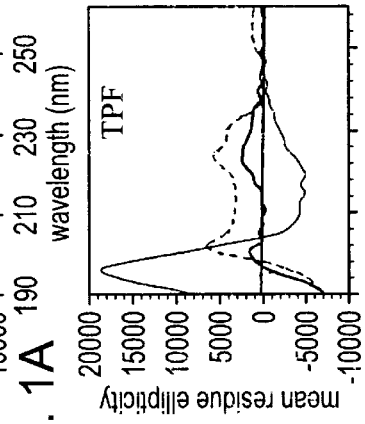
Fig. 1B TPF
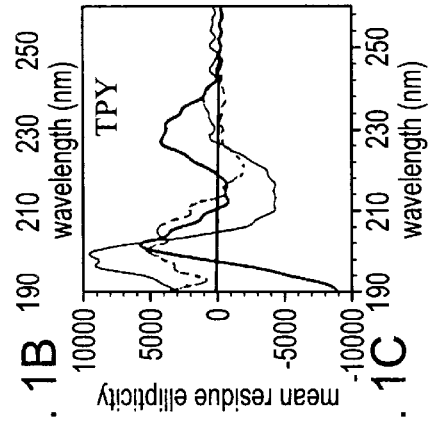
Fig. 1C TPY

PEPTIDE DERIVATIVES OF TACHYPLESIN HAVING ANTIMICROBIAL ACTIVITY

FIELD OF THE INVENTION

The invention relates to methods and compositions having antimicrobial activities. The compositions are useful in agricultural and medical applications.

BACKGROUND OF THE INVENTION

Plants and animals have to survive in a world laden with pathogenic, bacteria and fungi. Numerous fungi and bacteria are serious pests of both agricultural crops and mammals. Yet, despite the pathogens which are encountered daily, organisms display an uncanny survivability. The resilience displayed by diverse organisms can be attributed to the presence of a repertoire of host defense organisms.

In animals, including humans, defense may be mediated by events such as immune response, complement activation, phagocytosis, and release of small molecular weight antimicrobial peptides. I-lowever, in insects, amphibians, and other lower organisms, although comparable immune responses are less well characterized, it is clear that small molecular weight peptides play a major role in warding off infection.

Plants display apparent protective mechanisms in response to pathogens. Such responses include the production of proteins that alter extracurricular matrix of the host, such as extensins and glycine-rich proteins. Additionally, plants produce proteins that are directly involved with antimicrobial activity, such as glucanases and chitinases, protease inhibitors, and enzymes associated with phytoalexin biosynthesis.

Various antimicrobial peptides have been isolated from many different kinds of organisms, such as bacteria, insects, mammals, amphibians and plants. Examples include linear peptides, such as secropin, magainin and melittin, as well as tachyplesin, and members of the defensin family.

Tachyplesin is a naturally occurring cationic antimicrobial peptide that is seventeen (17) residues long. The peptide has an amidated carboxy terminus and contains two disulfide bridges. The antimicrobial activity of the molecule has been attributed to an amphipathic structure consisting of two anti-parallel P-sheets held ridged by the disulfide bonds and beta turn.

U.S. Pat. No. 5,580,852 discloses derivatives of the peptide tachyplesin which have potent anti-fungal activity against common plant pathogens. Specific amino acids sequences are set forth as having plant pathogenic fungi and seed pathogen activity. However, there is no method set forth in the application whereby amino substitutions can be made and activity predicted. In fact, there is no a priori method of predicting that any given protein will function. Each protein is unique, and this necessarily has to be an experimental determination. The scientific literature is replete with examples for seemingly conservative substitutions that have resulted in major perturbations of structure and activity.

Because of the pathogens facing both the plant and animal world, new antimicrobial peptides are needed. Furthermore, there is needed a method to predict the activity of new derivatives of tachyplesin proteins.

SUMMARY OF THE INVENTION

Compositions comprising antimicrobial peptides are provided. The peptides are derivatives of tachyplesin having amino acid substitutions in which the four cysteine residues are replaced with hydrophobic amino acids. The compositions are useful in methods of the control of fungal and bacterial activity in agricultural and medical applications.

Methods for making the purified compounds and use of such compounds are provided. Additionally, organisms, including plants and animals, containing or modified to contain, expression systems for the production of the peptides are provided.

BRIEF DESCRIPTION OF DRAWINGS

FIG. 1. Far UV CD spectra of peptides in water (thick line), 50% TFE (thin line) and 1 mM acidic liposomes (dashed lines). (A) TP (B) TPF (C) TPY (D) TPV (E) TPM (F) TPL (G) TPI (H) TPA (I) TPD.

DETAILED DESCRIPTION OF THE INVENTION

Figure 2:
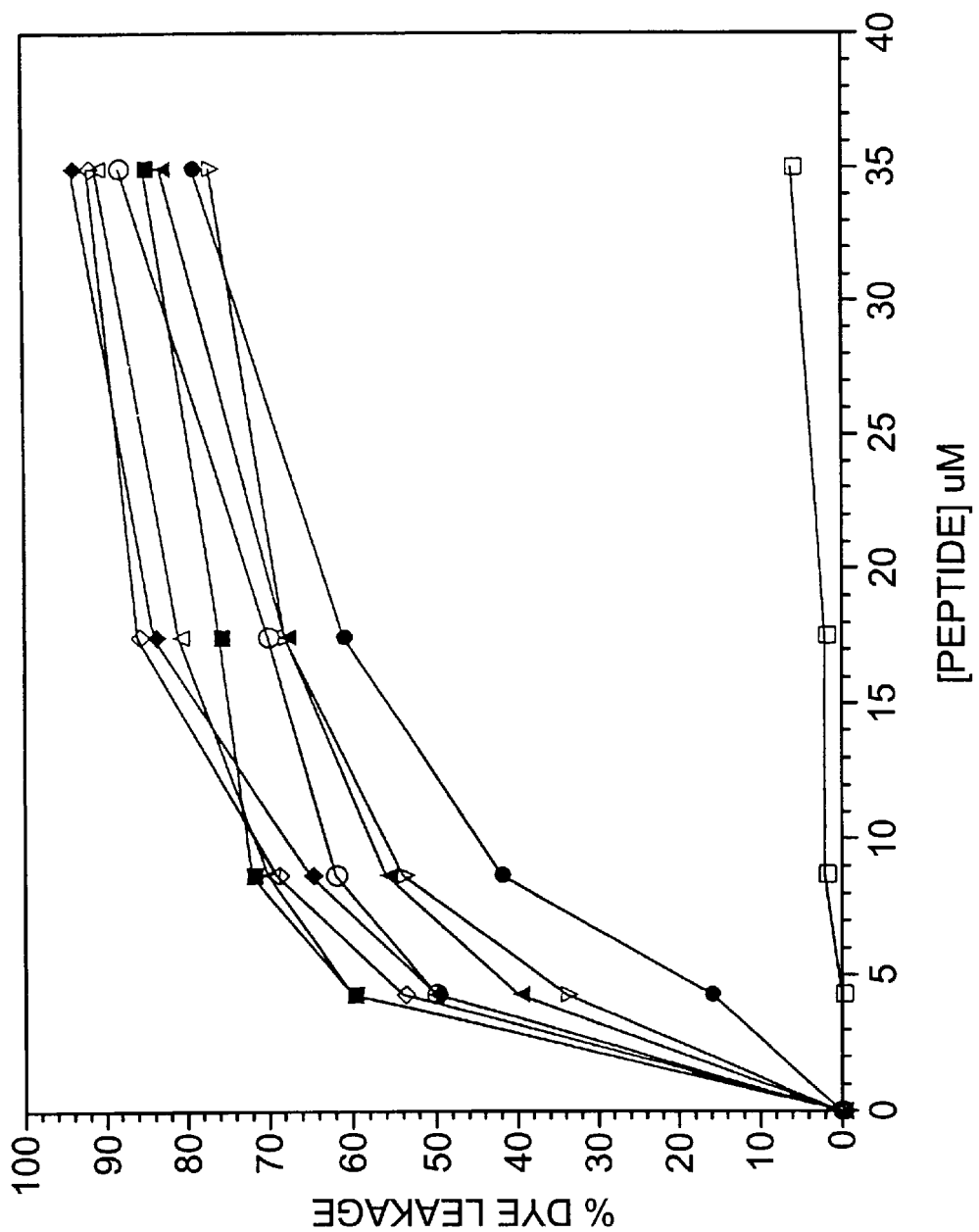
FIG. 2. Dye leakage of peptides from acidic liposomes (PC:PA, 3:1) as monitored by fluorescence intensity of released carboxyfluorescein. The maximum fluorescence intensity achieved with 0.1% Triton X-100 was considered to represent 100% cleavage and the efficiency of peptide induced release of dye was quantitated relative to this value (see materials and methods).
-○- TP, -●- TPA, -□- TPD, -■- TPF,, -◇- TPI, -◆- TPL, -▽- TPM, -Δ- TPV, -▲- TPY.

Compositions comprising antimicrobial peptides are provided. Antimicrobial is intended to mean any compound that displays the ability to destroy, kill, or inhibit the growth of bacterial and fungal cells. Generally, the peptides comprise about fifteen to about nineteen amino acids, preferably about sixteen to about eighteen amino acids, more preferably about seventeen amino acids. Generally, the peptides of the invention comprise the following formula SEQ ID NO: 2:

wherein $X_1$, $X_2$, $X_3$, and $X_4$ are hydrophobic amino acids selected from the group consisting of isoleucine, valine, methionine, leucine, phenylalanine, tyrosine, but where $X_{1-4}$ cannot be leucine at each occurrence.

As discussed above, U.S. Pat. No. 5,580,852 discloses derivatives of tachyplesin. Sequence I.D. No. 19 includes the formula of the invention having leucine at each X occurrence. Accordingly, the present invention does not encompass such disclosed peptide.

The disclosure of the derivative having leucine substituted for cysteine at each occurrence, does not anticipate nor render obvious the present invention which excludes such peptide. In fact, there is no teaching in U.S. Pat. No. 5,580,852 that the cysteine residues could be substituted with the amino acids listed above. In fact, it was not until the present invention that such a prediction could be made.

The C-terminus of the constructed peptide of the invention may be in the form of the underivatized carboxyl group, either as the free acid or an acceptable salt such as the potassium, sodium, calcium, magnesium or other salt, of an inorganic inion or of an organic ion. The carboxyl terminus may be derivatized by the formulation of an ester with an alcohol at the formula Roh, or may be amidated by an amine of the formula $NH_3$, or $RNH_2$ or $R_2NH$, wherein each R is independently hydrocarbonyl of 1–6 C esterify above. Amidated forms of the peptides where the C-terminus has the formula $CONH_2$ are preferred.

The peptides of the invention have the cysteine residues replaced with a hydrophobic amino acid or a negatively charged amino acid. As discussed above, except in the case of leucine, the amino acids substituted for each cysteine residue may be the same, a different residue or any combination thereof.

Standard methods of synthesis of peptides are known in the art. See, generally, Rao et al. (1992) *Int. J. Peptide Protein Res.* 40: 507–514. Most commonly used techniques are solid phase synthesis techniques: indeed, automated equipment for systematically constructing peptide chains can be purchased. Solution face synthesis can also be used. When synthesized using the standard techniques, amino acids not encoded by the gene and D-enantiomers can be employed in the synthesis. Thus, one very practical way to obtain the compounds of the invention is to employ the standard chemical synthesis techniques.

The peptides of the invention comprise activity against pathogens, including fungal pathogens, microorganisms, viruses and the like. Viruses include any plant virus, such as tobacco or cucumber mosaic virus, ringspot virus, necrosis virus, maize dwarf mosaic virus, etc. Some of the fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakospora pachyrhizi, Pythium aphanidermalum, Pythium ultimum, Pythium debaryanum,* Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronosporaparasitica, Fusarium roseum, Alternaria alternata*; Alfalfa: *Clavibacter michiganese* subsp. *insidiosum, Pythium ultimum, Pythium irregulare, Pythium splendens, Pythium debaryanum, Pythium aphanidermatum, Phytophihora megasperma, Peronospora trifoliorum, Phoma medicaginis* var. *medicaginis, Cercospora medicaginis, Pseudopeziza medicaginis, Leptotrochila medicaginis, Fusarium oxysporum, Rhizoctonia solani, Uromyces strialus, Colletotrichum trifolii* race 1 and race 2, *Leptosphaerulina briosiana, Stemphylium botryosum, Stagonospora meliloti, Sclerotinia trifoliorum,* Alfalfa Mosaic Virus, *Verticillium albo-atrum, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia strinformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella zeae, Colletotrichum graminicola, Cercospora zeaemaydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudomonas avenae, Erwinia chrysanthemi* pv. *zea, Erwinia corotovora,* Cornstunt spiroplasma, *Diplodia macrospora, Sclerophthora macrospora, Peronosclerospora sorghi, Peronosclerospora philippinensis, Peronosclerospora maydis, Peronosclerospora sacchari, Spacelotheca reiliana, Physopella zeae, Cephalosporium maydis, Caphalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternate, Bipolaris sorghicola, Helminthosporium sorghicola, Curvularia*

*lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Of particular interest are the following group of plant and seed pathogenic fungi and seed pathogen: *Fusarium Graminearum, Fusarium Moniliforme, Sclerotinia Sclerotioroum, Sclerotinia Terifoliorum,* and *Aspergillus Flavus.* These fungi have significant economic impact. They produce crop losses through ear mold damage, and are also responsible for contamination of grain with alflatoxins and fumonisins.

Such pathogens may be inhibited or killed by introducing into the environment of the pathogen an antimicrobial amount of one or more peptides of the invention. Inhibition is defined as a reduction in the growth and/or reproduction of the microorganism according to standard measurements, such as the initial Minimum Inhibitory Concentration, or MIC. The MIC is the minimum concentration of the peptide in the growth environment at which inhibition occurs. Reference may be had to standard published text such as *Antimicrobial Susceptibility Testing,* 3rd edition, written by the Staff of the National Committee for Clinical Standard (1991) and the multi-volume set *Performance Standards for Antimicrobial Susceptibility Tests* published by the same group: An *Manual of Clinical Microbiology,* 5th edition Balows, A. et.al. eds., pp 1059–1202 (American Society of Microbiology, Washington, D.C., 1991), the disclosures of which are herein incorporated by reference.

For the control of plant pathogens the compounds can be applied to plants by any method known in the art such as by spray, dust, or other formulation common to the microbial arts. In this manner, microorganisms may be genetically engineered to produce such peptide.

Alternatively, plants may be genetically engineered to produce the peptide. For convenience for expression in plants, the nucleic acid encoding the peptide or peptides of the invention can be contained within expression cassettes. The expression cassette will comprise a transcriptional initiation region linked to the nucleic acid encoding the peptide of interest. Such an expression cassette is provided with a plurality of restriction sites for insertion of the gene or genes of interest to be under the transcriptional regulation of the regulatory regions.

The transcriptional initiation region, the promoter, may be native or homologous or foreign or heterologous to the host. It could be the natural sequence or a synthetic sequence. By foreign is intended that the transcriptional initiation region is not found in the wild-type host into which the transcriptional initiation region is introduced.

The transcriptional cassette will include in the in 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens,* such as the octopine synthase and nopaline synthase termination regions. See also, Guerineau et al., (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acid Res.* 15:9627–9639.

Where appropriate, the gene(s) may be optimized for increased expression in the transformed plant. In this manner, the sequences can be synthesized using monocot, dicot or particular plant; i.e. maize, soybean, sorghum, wheat, etc., preferred codons for improved expression. Methods are available in the art for synthesizing plant preferred genes. See, for example, U.S. Pat. Nos. 5,380,831, 5,436, 391, and Murray et al. (1989) *Nucleic Acids Res.* 17:477–498, herein incorporated by reference.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) *PNAS USA,* 86:6126–6130); potyvirus leaders, for example, TEV leader (Tobacco Etch Virus) (Allison et al. (1986); MDMV leader (Maize Dwarf Mosaic Virus); *Virology,* 154:9–20), and human immunoglobulin heavy-chain binding protein (BiP), (Macejak, D. G., and P. Sarnow (1991) *Nature,* 353:90–94; untranslated leader from the coat protein mRNA of alfalfa mosaic virus (AMV RNA 4), (Jobling, S. A., and Gehrke, L., (1987) *Nature,* 325:622–625; tobacco mosaic virus leader (TMV), (Gallie, D. R. et al. (1989) *Molecular Biology of RNA,* pages 237–256; and maize chlorotic mottle virus leader (MCMV) (Lommel, S. A. et al. (1991) *Virology,* 81:382–385). See also, Della-Cioppa et al. (1987) *Plant Physiology,* 84:965–968. Other methods known to enhance translation can also be utilized, for example, introns, and the like. The expression cassettes may contain one or more than one nucleic acid sequences to be transferred and expressed in the transformed plant. Thus, each nucleic acid sequence will be operably linked to 5' and 3' regulatory sequences. Alternatively, multiple expression cassettes may be provided.

Generally, the expression cassette will comprise a selectable marker gene for the selection of transformed cells. Selectable marker genes are utilized for the selection of transformed cells or tissues. Such selectable marker genes are known in the art. See generally, G. T. Yarranton (1992) *Curr. Opin. Biotech.,* 3:506–511; Christopherson et al. (1992) *Proc. Natl. Acad. Sci. USA,* 89:6314–6318; Yao et al. (1992) *Cell,* 71:63–72; W. S. Reznikoff (1992) *Mol. Microbiol.,* 6:2419–2422; Barkley et al. (1980) *The Operon,* pp. 177–220; Hu et al. (1987) *Cell,* 48:555–566; Brown et al. (1987) *Cell,* 49:603–612; Figge et al. (1988) *Cell,* 52:713–722; Deuschle et al. (1989) *Proc. Natl. Acad. Aci. USA,* 86:5400–5404; Fuerst et al. (1989) *Proc. Natl. Acad. Sci. USA,* 86:2549–2553; Deuschle et al. (1990) *Science,* 248:480–483; M. Gossen (1993) PhD Thesis, University of Heidelberg; Reines et al. (1993) *Proc. Natl. Acad. Sci. USA,* 90:1917–1921; Labowetal. (1990) *Mol. Cell Bio.,* 10:3343–3356; Zambretti et al. (1992) *Proc. Natl. Acad Sci. USA,* 89:3952–3956; Baim et al. (1991) *Proc. Natl. Acad. Sci. USA,* 88:5072–5076; Wyborski et al. (1991) *Nuc. Acids Res.,* 19:4647–4653; A. Hillenand-Wissman (1989) *Topics in Mol. and Struc. Biol.,* 10:143–162; Degenkolb et al. (1991) *Antimicrob. Agents Chemother.,* 35:1591–1595; Kleinschnidt et al. (1988) *Biochemistry,* 27:1094–1104;

Gatz et al. (1992) *Plant J.,* 2:397–404; A. L. Bonin (1993) PhD Thesis, University of Heidelberg; Gossen et al. (1992) *Proc. Natl. Acad. Sci. USA,* 89:5547–5551; Oliva et al. (1992) *Antimicrob. Agents Chemother.,* 36:913–919; Hlavka et al. (1985) *Handbook of Exp. Pharmacology,* 78; Gill et al. (1988) Nature 334:721–724; DeBlock et al. (1987) *EMBO J.,* 6:2513–2518; DeBlock et al. (1989) *Plant Physiol.,* 91:691–704; Fromm et al. (1990) 8:833–839; Gordon-Kamm et al. (1990) 2:603–618. Such disclosures are herein incorporated by reference.

A number of promoters are known in the art and may be used in the invention. Such promoters include, but are not limited to nos, ocs, napin, phaseloin, CaMV, and the like. It may be preferable to express the peptides from a pathogen inducible promoter. In this manner, damage is minimized to host cells until pathogen invasion.

The invention also provides methods of treating and preventing infection by susceptible organisms in an human or animal host in need of such treatment. Such treatment may comprise administration to the mammal host in need of such treatment a therapeutically effective amount of a peptide of the invention, or a composition comprising one or more of the peptides. The peptides may be administered parenterally, by inhalations spray, rectally or topically in dosage unit formulations containing conventional nontoxic, pharmaceutically acceptable carriers, adjuvants and vesiculas as desired. The term "parenterally" as used herein includes a subcutaneous, intravenous, intramuscular, intraarticular and intrathecal injection and infusion techniques. See, *Remington's Pharmaceutical Sciences,* latest edition, Mack Publishing Company, Easton, Pa.

Formulations of the present invention may comprise sterile aqueous and non-aqueous injection solutions of the active compound. Preparations should be isotonic with the blood of the intended recipient and essentially pyrogen free. These preparations may contain anti-oxidants, buffers, bacteriostats and solutes that render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use.

In the same manner, the peptide can be administered as a pharmaceutical formulation suitable for parenteral (e.g., subcutaneous, intradermal, intramuscular, intravenous and intraarticular), oral or inhalation administration. Alternatively, pharmaceutical formulations of the present invention may be suitable for administration to the mucous membranes of the subject (e.g., intranasal administration). The formulations may be conveniently prepared in unit dosage form and may be prepared by any of the methods well-known in the art.

Any inert pharmaceutically-acceptable carrier may be used, such as saline, or phosphate-buffered saline, or any such carrier in which the compositions of the present invention have suitable solubility properties for use in the methods of the present invention. Reference is made to Remington's Pharmaceutical Sciences, Merck Publishing Company Easton, Pa., Osol (ed.) (1980) for methods of formulating pharmaceutical compositions. The most suitable route of administration in any given case may depend upon the subject, the nature and severity of the condition being treated, and the particular active compound that is being used.

In the manufacture of a medicament according to the invention, the peptides are typically admixed with inter alia, an acceptable carrier. The carrier must, of course, be acceptable in the sense of being compatible with any other ingredients in the formulation and must not be deleterious to the patient. The carrier may be a solid or a liquid. One or more antimicrobial peptides may be incorporated in the formulations of the invention, which may be prepared by any of the well known techniques of pharmacy consisting essentially of admixing the components, optionally including one or more accessory therapeutic ingredients. Formulations of the present invention may comprise sterile aqueous and non-aqueous injection solutions of the active compound, which preparations are preferably isotonic with the blood of intended recipient and essentially pyrogen free. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use.

Typical daily dosage of the compound of the invention will vary depending upon the weight of the subject, the pathogen to be inhibited, the severity of the infection, and the like. Daily dose of the compounds of the invention administered to a host and single or divided doses may be in amounts, for example, from about 1 to about 2,000 mg/kg body weight daily and more usually about 50 to about 500 mg/kg. Dosage unit compositions may contain such amounts or fractions or sub-multiples thereof as appropriate to make up the daily dose. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

By "therapeutically effective amount" herein is meant an amount of either peptide or combination thereof sufficient to provide anti-fungal activity so as to alleviate or prevent infection by susceptible organisms in the human or lower animal being treated at reasonable benefit/risk ratio attended with any medical treatment.

Pharmaceutical compositions of the invention may comprise an effective amount of a compound in combination with a conventional pharmaceutical carrier. As used herein the term pharmaceutical carrier means a solid or liquid filler, diluent or encapsulating material. See, for example, U.S. Pat. No. 5,580,852, herein incorporated by reference.

Alternatively, the peptides may be expressed in the mammalian host. Vectors for gene delivery are available in the art and include SV40 virus (See, e.g., Okayama et al. (1985) *Molec. Cell Biol.* 5:1136–1142); Bovine papilloma virus (See, e.g., DiMaio et al. (1982) *Proc. Natl. Acad. Sci. USA* 79:4030–4034); adenovirus (See, e.g., Morin et al. (1987) *Proc. Natl. Acad. Sci. USA* 84:4626; Yifan et al. (1995) *Proc. Natl. Acad. Sci. USA* 92:1401–1405; Yang et al. (1996) *Gene Ther.* 3:137–144; Tripathy et al. (1996) *Nat. Med* 2:545–550; Quantin et al. (1992) *Proc. Natl. Acad. Sci. USA* 89:2581–2584; Rosenfeld et al. (1991) *Science* 252:431–434; Wagner (1992) *Proc. Natl. Acad. Sci. USA* 89:6099–6103; Curiel et al. (1992) *Human Gene Therapy* 3:147–154; Curiel (1991) *Proc. Natl. Acad. Sci. USA*

88:8850–8854; LeGal LaSalle et al. (1993) *Science* 259:590–599); Kass-Eisler et al. (1993) *Proc. Natl. Acad. Sci. USA* 90:11498–11502); adeno-associated virus (See, e.g., Muzyczka et al. (1994) *J. Clin. Invest.* 94:1351; Xiao et al. (1996) *J. Virol.* 70:8098–8108); herpes simplex virus (See, e.g., Geller et al. (1988) *Science* 241:1667; Huard et al. (1995) *Gene Therapy* 2:385–392; U.S. Pat. No. 5,501,979); retrovirus-based vectors (See, for example, Curran et al. (1982) *J. Virol.* 44:674–682; Gazitetal. (1986) *J. Virol.* 60:19–28; Miller, A. D. (1992) *Curr. Top. Microbiol. Immunol.* 158:1–24; Cavanaugh et al. (1994) *Proc. Natl. Acad. Sci. USA* 91:7071–7075; Smith et al. (1990) *Molecular and Cellular Biology* 10:3268–3271); herein incorporated by reference.

In the same manner, the peptides can be used in any mammalian expression vector. See, for example, Wu et al. (1991) *J. Biol. Chem.* 266:14338–14342; Wu and Wu (*J. Biol Chem.* (1988)) 263:14621–14624; Wu et al. (1989) *J. Biol. Chem.* 264:16985–16987; Zenke et al. (1990) *Proc. Natl. Acad. Sci. USA* 87:3655–3659; Wagner et al. (1990) 87:3410–3414.

Standard techniques for the construction of the vectors of the present invention are well-known to those of ordinary skill in the art and can be found in such references as Sambrook et al., *Molecular Cloning: A Laboratory Manual*, 2nd ed. (Cold Spring Harbor, New York, 1989). A variety of strategies are available for ligating fragments of DNA, the choice of which depends on the nature of the termini of the DNA fragments and which choices can be readily made by those of skill in the art.

The following examples are offered by way of illustration and not by way of limitation.

EXPERIMENTAL

Materials and Methods 1. Peptide design. Naturally occurring tachyplesin is a 17-residue peptide SEQ ID NO: 1 with the sequence KWCFRVCYRGICYRRCR in which the C-terminal residue is amidated and the four cysteines form two disulfide bonds (Nakamura et al. (1988) *J. Biol. Chem.* 263:16709–17713). However, in this study native tachyplesin (TP) refers to the peptide containing a carboxy terminal arginine residue. Eight linear derivatives were made in which the amino acid substitutions at the four cysteine residues (underlined) were identical but unique in each peptide i.e. TPA, TPL, TPI, TPV, TPM, TPF, TPY and TPD. The underscored letters signify the amino acid (in single letter code) substituting the four cysteine residues in the native peptide. The average molecular weight of these peptides was 2314.6 with T.P. being the lowest (2265 Daltons) and TRY being the highest (2423.8 Daltons). Some physic-chemical properties of the peptides such as relative hydrophobicity, net charge and hydrophobic moment are listed in Table 1.

2. Peptide Synthesis and Purification. Peptide synthesis was performed either on a model 431 A peptide synthesizer (Perkins-Elmer Applied Biosystems, Foster City, Calif.) or on a Rainin-Protein Technologies Symphony™ multiple peptide synthesizer (Rainin, Woburn, MA) with all solvents, reagents and FMOC amino acids derivatives being purchased from the respective companies. Peptides were synthesized using FastMoc™ chemistry involving [2-(1H-benzotriazol-1-yl)-1,1,3,3-tetramethyluronium hexafluorophosphate] (Hbtu) activation for coupling amino acids (Fields et al. (1991) *Peptide Research* 4:95–101) and 4-hydroxymethylphenoxymethyl-copolystyrene-21% divinylbenzene resin (HMP resin) for loading the C-terminal amino acid residue. Standard protecting groups were used on the reaction side chains: Glu, Asp (OtBu); Arg (Pmc); Lys, (Boc); His, Asn, (Trt); Try (tBu); Trp, (Boc). Cleavage and deprotection of peptides was performed as described by Rao et al. (1992) *Int. J. Peptide Protein Res.* 40:507–514. Folding and disulfide bond formation of native TPC was achieved by air oxidation of a solution of the crude peptide for 24 h at room temperature at a concentration of 0.1 mg/ml in 0.1M $NH_4HCO_3$ adjusted to pH 8.5 (Rao et al. (1992) *Int. J. Peptide Protein Res.* 40:507:514). Peptide purification was achieved by reversed-phase high pressure liquid chromatography using a Waters (Milford, Mass.) DeltaPak™ $_{18}$ column on a Waters 600 HPLC system. The fidelity of synthesis was confirmed by automated amino acid sequence analysis (Perkin-Elmer Applied Biosystems 477A protein sequencer), by amino acid analysis (Perkin-Elmer Applied Biosystems 420A derivatizer) and by MALDI mass spectroscopy.

3. Antifungal Assay. Assays for antifungal activity were performed as described in Duvick et al (1992) *J. Biol. Chem.* 267:18814–18820. Briefly, three maize fungal isolates, *Aspergillus flavus*, *Fusarium graminearum*, and *Fusarium moniliforme*, were obtained from the Pioneer Hi-Bred strain collection. Peptide stocks were prepared in water and filter sterilized. Peptide concentration was determined by UV absorbance (Scopes, R. K. (1974) *Anal. Biochem.* 59:277–282) and confirmed by amino acid analysis with >95% accuracy. Fungal spore suspensions were diluted to give a concentration of 250 spores/90 μl of dilute culture medium (0.037 gm NaCl, 0.0625 gm $MgSO_4 7H_2O$, 0.25 gm $Ca(NO_3)_2$, 2.5 gm glucose, 0.25 gm yeast extract, 0.125 gm Casein hydrolysate (enzyme) and 0.125 gm casein hydrolysate (acid) in 7.5 mM sodium phosphate buffer, pH 5.8. In a typical antifungal assay, serial dilutions of the peptide were prepared in the first five wells of a 96-well microtiter plates by making serial dilutions from 100 μg/ml to 3 μg/ml of the peptides prepared in buffer and filter sterilized. To this, 50 μl of culture medial (in a 4×concentration) and 50 μl of the bacterial strain (in the concentration of $10^5$ CFU/ml) were added and mixed. Assays were performed in duplicate for each peptide. After 20 hours of incubation at the optimal growing temperature, the optical density at 600 nm was read on an absorption microtiter plate reader (Molecular Devices Corp., Palo Alto, Calif.). Percentage inhibition was calculated as [1-(a/b)×100] where a=$OD_{600}$ of the bacteria with peptide and b=$OD_{600}$ of the control well containing only buffer, bacteria and media. The MIC value was defined as an inhibition of growth of >25% and the MCIC value was defined as 100% inhibition of growth 10 A subset of 7 peptides was also tested for activity against human pathogens such as *Salmonella typhimurium* (ATCC 13311), *Pseudomonas aeruginosa* (ATCC 21036), *Staphylococcus aureus* (ATCC 25923), *Shigella dysenteriae* (ATCC 13313) and *Candida albicans* (ATCC 10231) using the disk diffusion assay as described by the National Committee for Clinical Laboratory Standards (*National Committee for Clinical Laboratory Standards Document* M2-A5 (1993) 13:1–20). Mueller-Hinton agar plates (100 mm, pH 7.2) were prepared and inoculated by streaking with a sterile swab that was dipped in inoculum suspension adjusted to 0.5 McFarland turbidity standard from an overnight culture of the organism except for C. albicans which required 48 hours for good growth. Antimicrobial disks (l3mm) wee prepared by adding 100 μl aliquots of each peptide at concentrations of 1 mg/ml, 0.5 mg/ml and 0.3 mg/ml to individual disks. They were then dispensed on to the surface of the inoculated agar plate, the plates inverted and placed in an incubator set to 35° C. within 15 min after the disks were applied. Results were read 18 hours after the plates were incubated. Zones were measured to the nearest whole millimeter starting from the center of the disk. The zone margin was taken as the area showing no obvious, visible growth that could be detected with the unaided eye.

4. Hemolytic Activity Assay. The ability of the peptides to lyse erythrocytes (hemolysis) was examined with rabbit red blood cells in PBS, pH 7.2 as described by Young et al. (1986) *Anal. Biochem.* 154:649–654 and is based upon the differences in light scattering (turbidity) properties of intact and lysed erythrocytes. Rabbit red blood cells (Colorado Serum Company, Denver, Colo.) or human red blood cells (Biological Specialty Corporation, Colmar, Pa.) were centrifuged and washed three times in PBS buffer. Following the last wash, the cells were then suspended in an equal volume of buffer containing 1% collagen (Sigma Chemicals, St. Louis, Mo.). A series of two-fold dilutions of the peptides were prepared in PBS and aliquoted into a flat-bottomed 96-well microtiter plate. Appropriate amounts of erythrocyte suspension were added to each well containing the peptide solution to give a final concentration $2 \times 10^8$ cell/ml. After 40 minutes of incubation at 37° C., the absorbance at 650 nm was read on an absorption microtiter plate as described earlier. The percentage of lysis was obtained by comparing the decrease in absorbance at 650 nm with a previously established standard curve which shows a linear correlation between the percentage of hemolysis and the turbidity as a function of the ratio of intact and lysed red blood cells.

5. Effect of peptides against plant protoplasts. Protoplasts from the maize variety Black Mexican Sweet (BMS) were prepared using the method described by Chourney et al. (1981) *Theor. Appl. Genet.* 59:341–344. Briefly, callus cells were incubated in appropriate media containing 0.2% Pectolyase Y-23 and 1% Cellulase RS (Boerhringer Mannheim, Indianapolis, Ind.) for 1–2 hours until ~80% of the cells had been digested. The protoplasts were then filtered through a sterile 70 µm filter. The filtrate containing the protoplasts were sedimented by centrifugation at 500 rpm and the pelleted cells subsequently washed with media (10 gm $CaCl_2$, 0.976 gm MES, 54.66 gm mannitol per liter). This process was repeated three times. After the final wash, the cells were resuspended in 10 ml of liquid media. The cells were counted on a hemocytometer and prepared to a final concentration of $2 \times 10^5$ cells/ml. Subsequently, 25 µl of fluorescein diacetate (5 mg/ml in acetone) was added to 10 ml solution containing protoplasts. Under these conditions, viable cells take up fluorescein diacetate and fluoresce when excited by UV light (Widholm, J. M. (1972) *Stain Technology* 47:189–194). Aliquots (1 ml) of protoplasts were pipetted into a 24-well microtiter plate and serial dilutions of sterile peptide added to each well. The plate was then incubated at room temperature for four hours and the viable cells visualized under an inverted fluorescence microscope. Wells were scored based upon the following criteria: a score of "0" was given to a well which showed no visible difference in the number of viable cells as compared to the control wells containing no peptide, a score of "1" was given to wells which showed a 25% reduction in the number of viable cells, a score of "2" was given to wells which showed a 50% reduction in the number of viable cells, and a score of "4" was given to wells that contained no viable cells.

6. Membrane Perturbation. The ability of the peptide to perturb membranes was examined by quantitating the fluorescence of released dye from liposomes prepared as follows. Egg phosphatidylcholine (PC) and egg phosphatidic acid (PA) were obtained from Avanti Polar Lipids (Birmingham, Ala.). Carboxyfluoroscein entrapped liposomes were prepared in PBS, pH 7.4 as described previously (MacDonald el al. (1991) *Biochem. Biophys. Acta* 1061:297–303). Briefly, 20 mg of a mixture of PC:PA (3:1) in chloroform was dried under a stream of nitrogen and then lyophilized under a vacuum for at least one hour. The lipids were rehydrated in 2 ml of 100 mM carboxyfluoroscein in PBS, pH 7.4. Large unilamellar vesicles were produced by taking multilamellar vesicles through 10 cycles of freezing (liquid nitrogen) and thawing (10° C. water bath) followed by extrusion (15–29 cycles) through two 100 nm polycarbonate filters in a Lipofast extruder (Avestin, Inc., Toronto, Canada). The carboxyfluoroscein-encapsulated liposomes were passed through a Sephadex G-25 column equilibrated with PBS to separate the free dye from the liposomes. Final lipid concentrations were determined as a function of phosphorus concentration using the Wako reagent (Suenega et al. (1989) *Biochem. Biophys. Acta* 981:143–150). Aliquots of stock solutions of peptides prepared in PBS were added to 0.5 ml of liposome solutions to give varying ratios of lipid/peptide with the concentration of the liposome at 0.1 mg/ml. The samples were incubated at 23° C. for 20 min and the resulting peptide induced carboxyfluroscein leakage produced an increase in fluorescence. This was monitored on a Perkin-Elmer Model 50 luminescence spectrofluorimeter at an excitation wavelength of 490 nm and an emission wavelength of 515 nm. The maximum fluorescence intensity achieved with 0.1% Trion X-100 was considered to represent 100% leakage. The degree of leakage induced by each peptide was calculated using the equation: % leakage=$(F-F_0)/(F_t-F_0) \times 100$ where F is the fluorescence intensity achieved by the peptides, $F_0$ is the intensity observed without peptides, and $F_t$ is the fluorescence intensity observed after the addition of Trion X-100.

7. Cytotoxicity assay. Freshly harvested Hep-2 cells (Larynx carcinoma epithelial cells) were aliquoted into separate tubes at a concentration of $3 \times 10^4$/tube and incubated with peptide or PBS as control. Each peptide was used at two concentrations, 4.3 µM and 21.5 µM, and the assays were done in duplicate. Reaction was carried out at room temperature for 90 min. after which the reactants were transferred to a single well of 96 well tissue culture plate (Costar). The reaction was allowed to proceed for an additional 90 min. to allow the cells to adhere to the plate. Subsequently, the supernatant from each well was removed and the cytotoxicity/viability of the adhered cells was determined using the Eukolight kit (Molecular Probes, Eugene, Oreg.). Cells were incubated with 100 µl of ethidium homodimer:calcein AM mixture (0.5 µM) for 45 min at room temperature and then viewed under a fluorescence microscope. Following excitation at 485 nm, live cells appeared green when viewed through a 530 nm bandpass filter and dead cells appeared bright red when viewed through a 590 nm long-pass filter. Total number of fluorescent cells were counted and cytotoxicity (dead cells) expressed as a percentage of the total.

8. Circular dichroism (CD) measurements. The CD spectra of peptides in water, 50% TFE or liposome were recorded at 25° C. in the 190-260 nm range with a JASCO 600 spectropolarimeter using 0.1 cm cells. The protein concentration was 0.1 mg/ml and the contribution of the solvent to the spectra was electronically subtracted. Mean residue ellipticity (θ) was calculated using the molecular weight of each peptide as determined from the amino acid composition. The percentage of helicity was calculated according to the equation of % helix=$[\theta]_{222}/[\theta]_{max}$ where $[\theta]_{222}$ is the observed ellipticity at 222 nm and $[\theta]_{max}$ is the maximal theoretical ellipticity ($-33,528$ deg.cm$^2$.dmol$^{-1}$) expected for a 100% helical peptide of 17 residues (Chen et al. (1974) *Biochemistry* 13:3350–3359).

RESULTS

1. CD study. In work done previously, Kawano et al. (1990) *J. Biol. Chem.* 265: 15365–15367, have shown by NMR that the structure of tachyplesin consists of an antiparallel β-turn and held rigidly by two disulfide bonds. However, in the absence of constraints imposed by disulfide bonds, linear derivatives of the peptide are likely to be flexible in solution, adopting conformations dictated by the environment (Zhong et al (1992) *Proc. Natl. Acad. Sci. USA* 89:4462–4465; Li et al. (1993) *J. Biol. Chem.* 268:22975–22978). Therefore, it was of interest to determine the solution conformations of the linear peptides by CD spectroscopy especially since the popular algorithms for secondary structure prediction (Chou et al. (1978) *Annu. Rev. Biochem.* 47:251–256; Garnier et al. (1978) *J. Mol. Biol.* 120:97–120) indicated an overall propensity for P-sheet structures for all of the linear derivatives of TP.

The CD spectra of the peptides in water, 50% TFE and acidic liposomes was examined. Trifluoroethanol has been widely used in protein structure studies since it can induce the adoption of stable, protein-like conformations from otherwise unstructured peptides in aqueous solution (Kim et al. (1982) *J. Mol. Biol.* 162:187–199; Marion et al. (1988) *FEBS Lett.* 227:21–26; Yamamoto et al. (1990) *Biochemistry* 29:8998–9006). In water, the spectrum of TP (FIG. 1A) is similar to that reported by other researchers (Park et al. (1992) *Biochemistry* 31:12241–12247; Tamamura et al. (I 993) *Chem. Pharm. Bull* 41:978–980). It shows a negative minimum around 208 nm and a positive peak at ~198 nm. Also seen is a strong positive band in the 228–230 nm range that may be attributed to the β-turn of the protein (Chang et al. (1978) *Anal. Biochem.* 91:13–17). Therefore, given that the NMR structure of TP indicates an ordered β-pleat sheet structure, the observed CD spectrum may be considered as representative of this structure. Furthermore, if the molecule is rigid, it would be expected to be resistant to any major solvent-induced conformational changes, and this is supported by the relatively minor changes in the CD spectrum in TFE and acidic liposomes.

However, the spectra of the linear forms appeared to be related to the nature of the amino acid used to replace the cysteine residues. For example, when compared to the CD spectrum of TP in water, the tyrosine derivative (TP$\underline{Y}$) is more similar to the wild-type peptide than the phenylalanine derivative (TP$\underline{F}$) (FIG. 1B and 1C). However, in the presence of TFE, the derivatives show very similar spectra with a broad minima in the 216–220 nm region and a positive band between 195 and 200 nm that is described as being characteristic of a β-pleated sheet structure (Greenfield et al. (1969) *Biochemistry* 8:4108–4116). Although the effect of TFE on such structures is less clear, there are examples of TFE induced β-sheet stabilization amongst similarly sized peptide fragments (Lu et al (1984) *J. Biol. Chem.* 259:7367–7370; Marenson et al. (1985) *Biochemistry* 24:7689–7695). Furthermore, it should be noted that minor differences in curve shapes and intensities can also arise from the contributions of aromatic side-chains in the far-UV range of the spectrum (Hooker el al. (1970) *Biopolymers* 9:1319–1348; Strickland et al. (1976) *Biochemistry* 15:3875–3884; Strassburger et al. (1982) *FEBS Lett.* 139:295–299. This is especially pronounced in molecules containing clusters of aromatic amino acids (Manning et al. (1989) *Biochemistry* 28:8609–8613). Indeed, in both 1TP$\underline{Y}$ and TP$\underline{F}$, the sequence contains clusters of aromatic amino acids at residues 2–4, 7–8 and 12–13. As compared to the spectra in TFE and water, the effect of acidic liposomes is more ambiguous. It appears that in the absence of the constraining influence of the disulfide bonds, the linear peptides undergo subtle conformational changes upon interaction with the negatively charged lipids.

The derivatives containing the aliphatic hydrophobic amino acids i.e., leucine (TP$\underline{L}$), isoleucine (TP$\underline{I}$), valine (TP $\underline{V}$) and methione (TP$\underline{M}$) provided an interesting contrast in the effect of solvent on peptide conformation. Whereas all derivatives in water had a strong minima ~200 nm, in accordance with a predominantly unordered structure (FIG. 1D, 1E, 1F and 1G), the CD spectrum of TP$\underline{I}$ also showed an apparent shoulder at ~220 nm (FIG. 1G). Although this profile did not significantly change in the presence of 50% TFE, in the presence of acidic liposomes, the minimum at ~200 nm disappeared and was replaced by a CD spectrum with a trough in the 217–220 nm region, indicative of a major contribution from a β-sheet type structure. By comparison, derivatives TP$\underline{L}$, TP$\underline{V}$ and TP$\underline{M}$ in 50% TFE showed CD spectra that was red-shifted, with clearly observable double minima at $\mu$210 and 222 nm and a strong positive at ~193 nm (FIG. 1D, 1E and 1F). Since such a spectrum is characteristic of α-helical structures, and despite the difficulty of accurately measuring peptide secondary structure by CD spectroscopy (Woody, R. W. (1985) *The Peptides: Analysis, Synthesis, Biology* (Udenfriend, S., and Meienhofer, J., eds) Vol. 7, pp. 15–113, Academic Press, Orlando, Fla.), it may be reasonable to conclude that the presence of TFE increases the proportion of helical conformation in these peptides at the expense of an unordered structure. Based on the ellipticity values at 222 nm, an α-helical content of 20–25% was calculated for these peptides. However, when measurements were made in buffer containing acidic liposomes, interesting differences were observed. The derivative TP$\underline{L}$ once again showed a CD profile characteristic of an a-helical structure but with a shallower trough in the 220 nm region and positive ellipticity values above 230 nm (FIG. 1F), whereas the TP$\underline{V}$ variant did not exhibit the α-helical profile observed in 50% TFE, the peptide in acidic liposomes nevertheless underwent a transition to some ordered structure, that perhaps included an α-helical contribution, as evidenced by the double minima at ~204 nm and 225 nm (FIG. 1D). Measurement with TP$\underline{M}$ could not be made owing to turbidity and consequent noisy spectrum in the presence of liposomes. On the other hand, while the variant containing the aliphatic amino acid with the shorter side-chain (TP$\underline{A}$) showed a typical random structure in water, 50% TFE and acidic liposomes (FIG. 1H), the aspartic acid (TP$\underline{D}$) derivative appeared to be able to adopt an a-helical configuration in all three solvents as judged by the apparent shoulder at ~225 nm (FIG. 1I).

Antimicrobial activity. With the exception of TP$\underline{A}$ and TP $\underline{D}$, measurable MIC and MCIC values were obtained for all of the peptides against the maize fungal pathogens *A. flavus, F. graminearurn* and *F. moniliforme* (Table 2). Indeed, the inhibitory activities of the linear derivatives peptides are similar to the cyclic peptide and even superior in some cases. The activity of the naturally occurring antimicrobial peptides cecropin B and mastoparan are also shown for comparison. Similarly, when tested against the Gram(−) negative bacteria *E. coli*, with the exception of peptides TP$\underline{A}$ and TP $\underline{D}$ that were unable to achieve MCIC levels, all the other peptide derivatives displayed activity profiles that were not dissimilar from that of the wild-type peptide.

Tachyplesin and the related peptides polyphemusins have been previously shown to be active against human pathogens such as the Gram(−) *S. typhimurium, P. aeruginosa*, Gram(+) *S. aures* and the fungus, *C. albicans* (Miyata et al.

(1989) *J. Biochem.* (Tokyo) 106:663–668). Table 3 summarizes the activities of the linear derivatives against these organisms and also includes another Gram(+) pathogen, *S. dysenteria*. With the exception of TP<u>D</u>, zones of inhibition were observed with TP and the derivatives TP<u>F</u>, TP<u>L</u>, TP<u>I</u>, TP<u>M</u> and TP<u>V</u>. Peptides TP<u>Y</u> and TP<u>A</u> were not tested.

Membrane perturbation effects. The effect of TP and derivatives on the integrity of a variety of membrane structures was examined using both synthetic liposomes and native cells such as maize protoplasts, erythrocytes and epithelial cells.

Perturbation of liposomes. The effect of TP derivatives on membrane permeability was investigated by dye leakage experiments using acidic liposomes (FIG. 2). The aspartic acid derivative, TP<u>D</u>, did not release any encapsulated carboxyfluorescein from the liposomes even up to a concentration of 10 $\mu$M. Further increasing the concentration to 35 $\mu$M caused <10% leakage after 20 min incubation. This observation compares favorably with the relative inactivity of this peptide in antimicrobial assays (Tables 2 and 3). In contrast, the wild-type peptide and the other derivatives were able to achieve 50% dye leakage at ~10 $\mu$M and ~80% leakage at 35 $\mu$M. Surprisingly, this was also true of TP<u>A</u> which was similar to TP<u>D</u> in its lack of antimicrobial activity (Tables 2 and 3). For a general description of lipid vesicles, see Styer's Biochmistry, $2^{nd}$ Edition.

Figure 3:
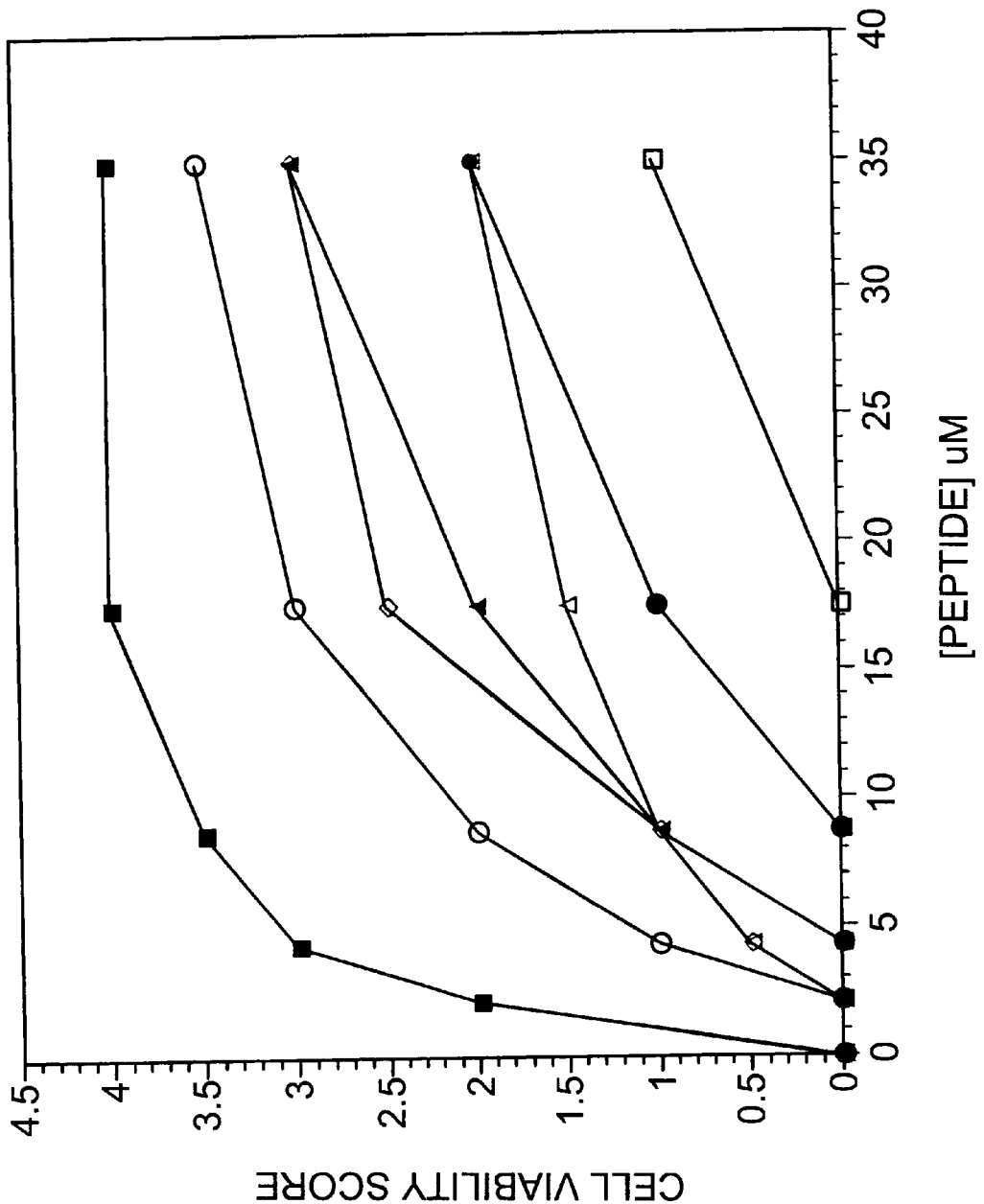
FIG. 3. Effect of peptides against maize protoplasts as measured by the ability of viable protoplasts to uptake fluorescein diacetate and visualized under an inverted fluorescence microscope. Protoplasts with damaged membranes are non-viable and therefore cannot uptake fluorescein diacetate. With added peptide, a score of "O" indicates that the number of viable cells is the same as the control, a score of "1" indicates that there is a 25% reduction in the number of viable cells, a score of "2" indicates a 50% reduction, a score of "3" indicates a 75% reduction and a score of "4" indicates a 100% reduction in the number of viable cells. -○- TP and TPM, -●- TPA and TPV, -□- TPD, -■- TPF,,-◇- TPI and TPL, -▲- TPY (see materials and methods for details).

Effect against maize protoplasts. As in the case with the liposomes, derivative TP<u>D</u> had relatively no effect on protoplast viability (FIG. 3). For all other derivatives, however, protoplast viability decreased as a function of increasing protein concentration and appeared to be dependent on the nature of the peptide. At the highest concentration used (35 $\mu$M), the toxicity of the peptides, as measured by cell viability, increased in the order TPF>TP/TPM>TPI/TPL>TPY>TPA/TPV and TPD.

The results described here clearly indicate that the linear derivatives of tachyplesin have antimicrobial properties. However, the mechanism of antimicrobial activity is unclear and more than likely involves membrane perturbation presumably from a high affinity interaction between the cationic peptides and negatively-charged phospholipids, lipopolysaccharides (LPS) and teichoic acid, which differ in gram-negative and gram-positive bacteria. Unlike the bacterial cells, however, the eukaryotic fungal cell is more complex and less well characterized. Although it is reasonable to expect differences in cell wall composition and structure among different fungal species, it is likely that here also the presence of negatively charged surface groups enable the pathogen to attract and attach to other molecules, including basic peptides. It is conceivable that the fungicidal action arises from the binding of cationic peptides to negatively charged head groups and eventual migration into the cell to disrupt the structural integrity of the cytoplasmic membrane. To this extent, although the effect of the peptides on plant protoplasts may be considered detrimental and contrary to their potential expression in plants, it should be considered in the context of the in vitro nature of the experiment. In an in vitro assay, it is not surprising that protoplasts are affected since the exterior face of the plasma membrane (being devoid of the cell wall) is exposed and can be disrupted like any other membrane (bacterial or fungal) upon interaction with an antimicrobial peptide. However, it is also important to realize that the biochemical nature of the plasma membrane is different on the inside and the outside. (Fredrikson et al. (1989) (Physiologia Plantarum 77, 196–201; Fredrikson et al. (1992) Transactions 20, 710–713; Johansson et al. (1995). Plant Journal 7, 165–173; Menendez et al. (1995) vesicles from *Saccharomyces cerevisiae*. Analytical Biochemistry 230, 308–314; Palmgren et al. (1990) detergents on the proton-ATPase activity of inside-out Biochimical Et Biophysica Acta 1021, 133–140; Pamgren et al. (1990) Plant Physiology 92, 871–880). Consequently, when the peptides are expressed within a plant cell it may be unreasonable to expect an interaction that would lead to the collapse of the plasma membrane. Therefore, the observed detrimental effect on plant protoplasts in an in vitro assay should not be construed as a barrier to the use of the peptides as in vivo agents of plant disease resistance.

Figure 4:
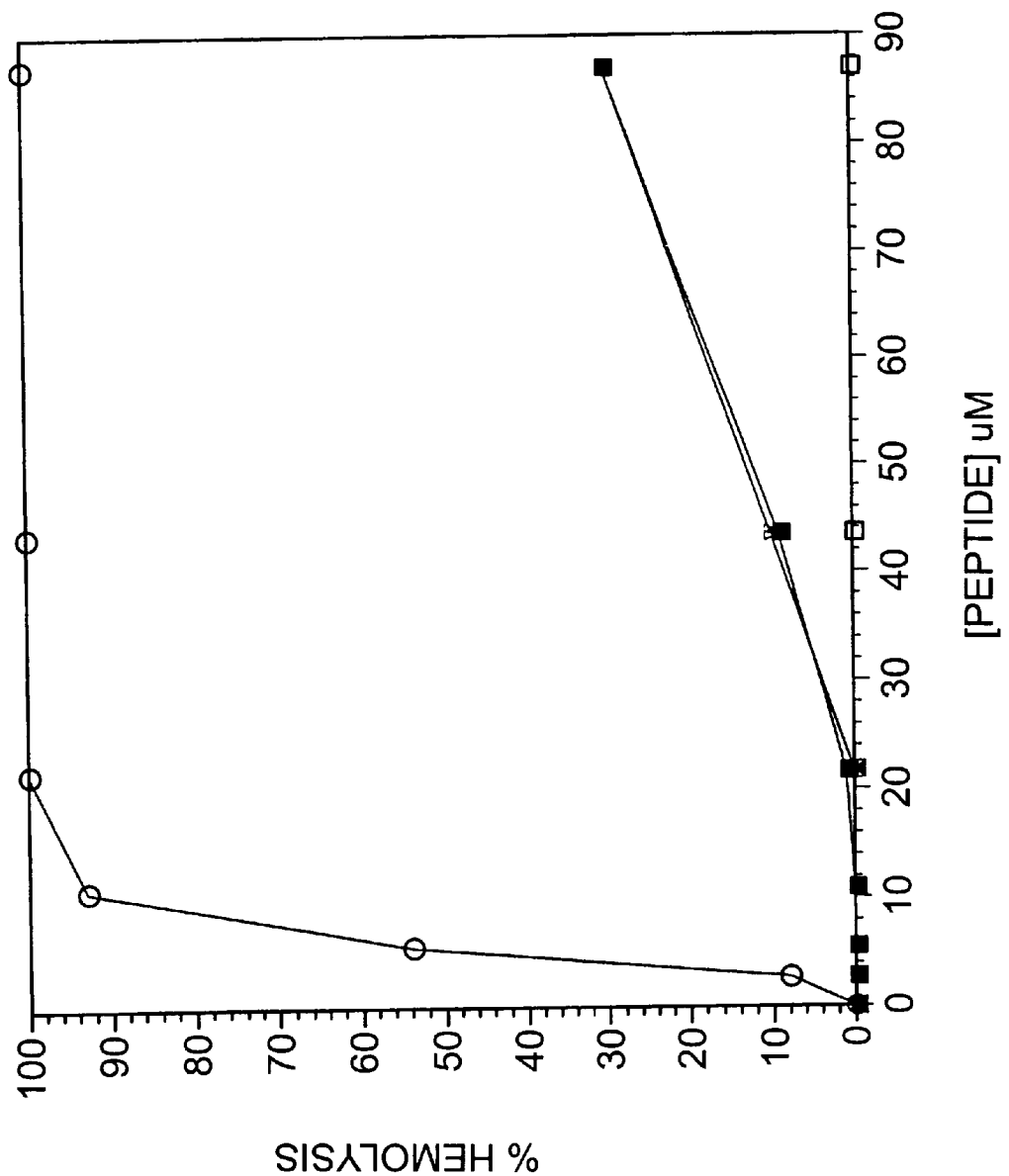
FIG. 4. Dose response curve of the hemolytic activity of the peptides towards rabbit erythrocytes. -○- Melittin, -□- TPD, -▽- TPM, -■- TPF, -▲- TPY.

Hemolytic activity. Concomitant to the design of antimicrobial peptides, is the goal of eliminating undesirable effects against mammalian cells especially for pharmaceutical applications. To this end, we investigated the effects of these peptides on rabbit erythrocytes. In contrast to the known hemolytic peptide, melittin, which showed complete lysis at ~10 $\mu$M, TP and derivatives displayed little or no activity at this concentration. Only about 30% lysis was observed with TP<u>M</u>, TP<u>F</u> and TP<u>Y</u> even at concentrations >80 $\mu$M (FIG. 4). In a separate experiment hemolytic activity of TP and amidated-TP (native TP with amidated carboxy terminal) was also measured using human erythrocytes. Flowever, in contrast to the results of Katsu et al., (1993) *Biol. & Pharm. Bullet.* 16:178–181, who observed 100% lysis with amidated-TP at 100 $\mu$M, we observed only about 30% hemolysis even at concentrations >100 $\mu$M. The activity of TP was only about 15% at equivalent concentrations (data not shown).

Effect against Hep-2 cells. The effect of these peptides was also measured against another class of mammalian cells i.e., larynx carcinoma epithelial cells (Hep-2). The toxicity, measured at concentrations of 4.3 $\mu$M and 21.5 $\mu$M (Table 4), indicated that the peptides were not significantly cytotoxic with approximately >80% of the cells being still viable at these concentrations.

TABLE 1

Relative Hydrophobicity and charge properties of tachyplesin and derivatives

| Peptide | Hydrophobicity[a] | Net Charge | $\mu_H$[b] (as $\alpha$-helix) | $\mu_H$[c] ($\beta$-sheet) |
|---|---|---|---|---|
| TP | −0.44 | +6 | | |
| TPA | −0.36 | +6 | 0.65 | 0.67 |
| TPD | −0.72 | +2 | | 0.87 |
| TPV | −0.26 | +6 | 0.71 | 0.60 |
| TPM | −0.36 | +6 | 0.65 | 0.66 |
| TPI | −0.19 | +6 | 0.74 | 0.56 |
| TPL | −0.26 | +6 | 0.70 | 0.61 |
| TPF | −0.23 | +6 | 0.72 | 0.59 |
| TPY | −0.45 | +6 | 0.62 | 0.72 |
| Melittin | +0.195 | +6 | 0.57 | |

[a]Mean hyrophobicity values calculated based on the normalized consensus scale values of Sweet & Eisenberg (66).
[b,c]Hydrophobic moment, $\mu_H$, calculated by the method of Eisenberg et al., (1984), as an $\alpha$-helix or a $\beta$-sheet, for a moving window of 11 residues. The highest value was for the segment comprising residues 1 through 12 of each sequence and these are represented as a mean for windows 1 to 11 and 2 to 12. For melittin the value is for residues 12 through 22 of the sequence.

TABLE 2

Antimicrobial activity. In vitro susceptibility of maize fungal pathogens and E. coli to tachyplesin and derivatives. For E. Coli, MIC is defined as the minimum inhibitory concentration to achieve 25% growth inhibition and MCIC is the minimum complete inhibitory concentration to achieve 80% or greater growth inhibition. See materials & methods for MIC/MCIC definitions for the fungal pathogens. Results are an average of two independent measurements with a standard deviation of 15%.

| PEPTIDE | A. flavus MIC/MCIC $\mu$M | F. graminearum MIC/MCIC $\mu$M | F. moniliforme MIC/MCIC $\mu$M | E. coli MIC/MCIC $\mu$M |
|---|---|---|---|---|
| TP | 13/34 | 8/17 | 8/21 | 1/3 |
| TPD | >35/>35 | >35/>35 | >35/>35 | 22/>35 |
| TPA | >35/>35 | >35/>35 | >35/>80 | 3/>35 |
| TPF | 13/17 | 10/13 | 4/8 | 1/6 |
| TPY | 8/22 | 7/9 | 4/8 | 1/3 |
| TPL | 8/35 | 7/9 | 6/9 | 1/11 |
| TPI | 35/>35 | 12/17 | 12/17 | 1/11 |
| TPM | 17/>35 | 6/8 | 6/8 | 1/6 |
| TPV | 17/>35 | 6/9 | 6/9 | 1/6 |
| cecropin B | >20/>20 | 3/5 | 3/20 | NA |
| mastoporan | 24/>50 | 5/8 | 3/11 | NA |

TABLE 3

Antibacterial activity of tachyplesin and derivatives against human pathogens as measured by the zone of inhibition (in mm) in a disk diffusion assay (see material and methods).

| Peptide | S. typhimurium 100 $\mu$g zone size (mm) | S. typhimurium 50 $\mu$g zone size (mm) | P. aeruginosa 100 $\mu$g zone size (mm) | P. aeruginosa 50 $\mu$g zone size (mm) | S. aureus 100 $\mu$g zone size (mm) | S. aureus 50 $\mu$g zone size (mm) | S. dysenteria 100 $\mu$g zone size (mm) | S. dysenteria 50 $\mu$g zone size (mm) | C. albicans 100 $\mu$g zone size (mm) | C. albicans 50 $\mu$g zone size (mm) |
|---|---|---|---|---|---|---|---|---|---|---|
| TP | 18 | 18 | 14 | 14 | 18 | 18 | 18 | 18 | 16 | 16 |
| TPF | 18 | 17 | 18 | 17 | 18 | 17 | 19 | 19 | 18 | 18 |
| TPL | 18 | 17 | 17 | 17 | 17 | 16 | 17 | 16 | 17 | 16 |
| TPI | 17 | 16 | 14 | 14 | 17 | 14 | 17 | 14 | 17 | 15 |
| TPM | 17 | 16 | 16 | 16 | 16 | 15 | 16 | 15 | 16 | 16 |
| TPV | 16 | 16 | 20 | 20 | 15 | 15 | 16 | 15 | 17 | 16 |
| TPD | no zones | | no zones | | no zones | | no zones | | no zones | |

TABLE 4

Cytotoxicity of peptides to Help-2 cells (Larynx carcinoma epithelial cells). Cytotoxicity is expressed as a percentage of dead cells as determined by differential fluorescence of living and dead cells (see materials and methods). Results are given as a mean of two experiments ± standard deviation.

| Peptide | % cytotoxicity 4.3 $\mu$M | % cytotoxicity 21.5 $\mu$M |
|---|---|---|
| TP | 12.0 ± 0.9 | 23.9 ± 1.5 |
| TPY | 19.7 ± 2.9 | 22.6 ± 2.0 |
| TPF | 30.8 ± 2.8 | 27.0 ± 1.1 |
| TPL | 20.1 ± 3.1 | 18.4 ± 6.7 |
| TPI | 16.0 ± 0.6 | 31.3 ± 1.5 |
| TPM | 14.2 ± 3.1 | 18.8 ± 1.8 |
| TPV | 14.6 ± 1.8 | 14.3 ± 2.1 |
| TPD | 17.7 ± 0.73 | 22.7 ± 3.7 |
| TPA | 17.5 ± 1.3 | 21.9 ± 4.3 |

DISCUSSION

The first study establishing a link between the structure and antimicrobial activity of TP came from the experiments of Tamamura et al., (1993) Chem. Pharm. Bull. 41 :978–980, who synthesized linear derivatives of TP in which the four cysteines were either chemically modified with acetamidomethyl (Acm) group or were replaced with Ala. The CD spectra of these linear peptides in water corresponded to random-coiled structures and their antimicrobial activity against both classes of bacteria was significantly reduced in comparison with the disulfide bonded TP, suggesting that the β-sheet structure maintained by disulfide bridges was indeed important to the antimicrobial activity. The latter conclusion was supported by the experiments of Park et al., (1992) Biochemistry 31:12241–12247, who, however, observed that the CD spectrum of the linear Acm derivative was not appreciably different from that of the native TP in aqueous solution. They concluded that the primary sequence of TP encoded information for the secondary structure that was independent of the presence or absence of disulfide bonds.

Inasmuch as these experiments attest to the potential importance of the disulfide bond in the structure-function relationship of tachyplesin, the conclusions are narrow, and the results may be specifically attributed to the physico-chemical properties of one amino acid side-chain i.e. alanine. However, it is widely accepted in protein science that the conformation of a polypeptide is ultimately a function of the geometry and chemistry of the amino acid side-chains, their interactions with the polypeptide backbone and the solvent environment (Richardson et al. (1989) in Prediction of Protein Structure and the Principles of Protein Conformation (Fasman, G. D., ed.), pp. 1–98, Plenum Press, New York & London). In addition, the amino acid sequence of a given protein may be highly degenerate to the extent that many different sequences may still preserve the essential structure-function relationship of the protein (Bowie et al. (1990) Science 247:1306–1310). Therefore, a more global perspective on the tolerance of cyst(e)ine residues in tachyplesin to amino acid substitutions may be gained from analyzing variants containing residues with different side-chain properties.

In this regard, it is relevant to consider the structure of tachyplesin itself. The NMR derived structure Kawano et al. (1990) J. Biol. Chem. 265:15365–15367 and Tamamura et al. (1993) Chem. Pharm. Bull. D41:978–980 indicates that the disulfide bonds, which link the two antiparallel β-sheets, are shielded from the aqueous environment, as is commonly the case for a majority of disulfide bond containing proteins (Thornton, J. M. (1981) J. Mol. Biol. 151:261–287). Furthermore, since core residue positions are extremely important for protein folding and stability, and are primarily composed of Ala, Val, Ile, Leu, Met, Phe, Cys and Thr (Bowie et al (1990) Science 247:1306–1310; Baldwin et al (1994) *Curr. Opin. Biotech.* 5:396–402), a priori, we postulated that the replacement of the cystine bond with hydrophobic side-chains may restore peptide conformation and stability through hydrophobic interactions, albeit in a non-covalent manner.

To this extent, a correlation of these postulates to experimental observations provides interesting insights into the structure-activity relationships in tachyplesin. From a secondary structure point of view, the CD spectra indicated a singular role for each of the amino acids used in the substitution of cysteines (FIG. 1). Whereas the small hydrophobic amino acid Ala, with its methylene side-chain, does not seem capable of allowing an ordered conformation, the other hydrophobic amino acids showed distinct effects in their facilitation of an ordered structure. For example, replacement with the aromatic amino acids, Phe and Tyr, resulted in derivatives that adopted conformations not too dissimilar to that of the native TP in 50% TFE although significant conformational change was indicated in acidic liposomes. A plausible explanation is that these residues have a high propensity to occur in β-strands and since the sequence corresponding to the turn region, YRGI, has not been altered, the linear peptides may indeed fold into a native-like TP structure, albeit stabilized by hydrophobic interactions within the core.

The preeminent role of the side-chain in influencing the structure of the peptides is further illustrated in the differences in the conformational properties of TP derivatives incorporating the aliphatic hydrophobic amino acids Leu, Ile, Val and Met. Those amino acids are fairly ambiguous in their preference for secondary structures, occurring frequently in either α-helics or β-strands (Richardson et al (1989) in *Prediction of Protein Structure and the Principles of Protein Conformation* (Fasman, G. D., ed.) Pp. 1–98, Plenum Press, New York and London). However, in contrast to the aromatic residues, a preferred tendency for the α-helical conformation was clearly evident in the variants containing Leu, Val and Met substituents, when measured in 50% TFE (FIGS. 1D, 1E and 1F). Even though the characteristic CD spectrum of α-helical structures was less pronounced in the presence of liposomes, the red shift in the spectrum for TP$\underline{V}$ and TP$\underline{L}$ clearly reflect an increase in the proportion of a certain ordered structure. There is no obvious explanation for the significantly different conformational behavior of the Ile derivative. However, based on the likeness of Ile and Val, in that both are branched at the β-carbon atom, a similar CD profile for TP$\underline{V}$ and TP$\underline{I}$ would have been more than a reasonable expectation.

These results once again reiterate the complex relationship between protein conformation and the role of individual amino acids in relation to rest of the polypeptide sequence and the solvent environment. This is especially meaningful in light of the recent work of Dalal et al., (1997) *Nat. Struct. Biol.* 4:458–552, who converted a sequence that folded as a β-sheet into a four helix bundle by making amino acid changes that still preserve 50% sequence identity. Additionally, it is worth noting that in aqueous solutions, protein secondary structures are in dynamic equilibrium, and it may not always be possible to delineate these various forms from CD data alone (Ilyina et al. (1995) *Biochem J.* 306:407–419; Woody, R. W. (1985) in *The Peptides. Analysis, Synthesis, Biology* (Udenfriend, S. and Meienhofer, J., eds) Vol. 7, pp. 15–113, Academic Press, Orlando, Fla.). Therefore, it may be erroneous to ignore the existence of other ordered structures such as the β-sheet. The calculated value for α-helical structures (~20%) is derived from the ellipticity at 222 nm, and since there is a strong overlap in the CD profiles of α-helics and β-sheets, it is difficult to measure the contribution from the latter type structure in an unambiguous manner. In this regard, it is reasonable to conclude that the CD spectrum of TP$\underline{I}$ may reflect the existence of both types of structures.

The antimicrobial properties of the linear peptides must, therefore, be determined by factors other than solely a shared structure. Several studies have indicated that two recurring themes in the structure-function properties of antimicrobial peptides are their amphipathy and their highly cationic nature (Lear et al. (1988) *Science* 240:1177–1181; DeGrado et al. (1981) *J. Am. Chem. Soc.* 103:679–681; Zasloff et al (1988) *Proc. Natl. Acad. Sci. USA* 85:910–913; Fink et al. (1989) *Int. J. Peptide Protein Res.* 33:412–421; Bowman et al. (1989) *FEBS Lett.* 259:103–106; Wade et al. (1992) *Int. J. Peptide Protein Res.* 40:429–436; Andreu et al (1992) *FEBS Lett.* 296:190–194; Zhong et al. (1995) *Int. J. Pept. Protein Res.* 45:337–347). One measure of the amphipathy of a given peptide is the hydrophobic moment $\mu_H$ (Eisenberg et al. (1984) *J. Mol. Biol.* 179:125–142). To this extent, $\mu_H$ of the linear derivatives (Table 1), whether modeled as α-helices or β-strands, are consistent with the values determined for other antimicrobial peptides (Zhong et al. (1995) *Int. J. Pept. Protein Res.* 45:337–347). This indicates that in an amphipathic environment, such as provided at the interface of lipid membranes, the linear peptides have the ability to fold into an amphipathic structure. Thus, although not intrinsically amphipathic in the fashion that the disulfide-bonded TP is, the linear derivatives clearly have the potential to adopt an amphipathic structure that may serve a mechanistic role in their activity. However, the overall charge and hydrophobicity of the molecule must also play a very critical role (Table 1) in concert with the biochemical nature of the interacting membrane.

The dye-release experiment with acidic liposomes (FIG. 2), but not with neutral liposomes (data not shown), attests to the importance of preliminary electrostatic interactions for membrane perturbation. A notable exception to the generally comparable membranolytic ability among the peptides is the variant TP$\underline{D}$, which has a reduced overall charge of +2 (Table 1) and causes little or not dye leakage at a peptide concentration of 35 $\mu$M. The four negative charges from the aspartate side-chains appear to exert a destabilizing effect on the interaction of the peptide with the membrane surface. Electrostatic interactions must also dominate the effect of these peptides on maize protoplasts (FIG. 3), although there is more of a gradation in the observed effects. However, here also TP$\underline{D}$ has little effect on cell viability at the highest concentration tested (35 $\mu$M). It appears that, while peptide hydrophobicity may not be a dominant factor in the interaction with synthetic, negatively charged membrane surfaces, it may contribute to some extent in the effect against maize protoplasts. Additionally, the bulkiness of the non-polar face may also be important and might help explain why TPA, with the smallest hydrophobic side-chain, is the weakest peptide after TP$\underline{D}$.

On the other hand, recent studies (Oren et al. (1997) *J. Biol. Chem.* 272:14643–14649; Wieprecht et al. (1997) *Biochemistry* 36:6124–6132) have established a strong correlation between relative hydrophobicity and hemolytic activity of peptides. Erythrocyte membranes contain predominantly zwitterionic phospholipids and little or no negatively charged lipids that would facilitate interaction with the positively charged peptides. Under these circumstances, hydrophobic interactions dictate the hemolytic activity of the peptide and, all other properties being equivalent, the greater the hydrophobicity of a peptide the greater is the expected degree of hemolytic activity. Thus, melittin with a relative hydrophobicity of +0.195 is a potent hemolytic agent while the TP derivatives which have negative hydrophobicity values are fairly innocuous to erythrocytes (Table I and FIG. 4) and are mildly cytotoxic to another class of eukaryotic cells, the larynx carcinoma epithelial cells (Table 4). This might suggest that the latter class of cells has a membrane lipid composition that is more conducive to electrostatic interactions with cationic peptides than permitted by the erythrocyte membranes.

TP shows comparable bactericidal activities against both Gram(+) and Gram(−) bacteria. As is the case with many typical antimicrobial peptides, the peptide is rich in basic amino acids. Presumably, the cationic nature confers a high affinity for negatively charged cell surface components such as the lipopolysaccharides (LPS) on the outer membrane of Gram(−) bacteria and (lipo)teichoic acids in Gram(+) bacteria. Tamamura et al. (1993) *Chem. Pharm. Bull.* 41:978–980, have suggested that the rigid disulfide-bonded antiparallel β-sheet structure is essential for activity against Gram(−) bacteria but not for activity against Gram(+) bacteria. One major constituent of LPS is 1, 6 diglucoside-1, 4'-diphosphate glycolipid (Galanos et al. (1985) *Eur. J. Biochem.* 148:1–5) in which the two phosphate groups are about 6–8 Å apart. Tamamura et al. (1993) *Chem. Pharm. Bull.* 41:978–980, contend that this distance complements the geometry of the Arg residues in the disulfide-constrained structure, and that it facilitates the initial binding of the amphipathic β-sheet peptide with the cell surface followed by membrane perturbation. Ohta et al. (1992) *Antimicrob. Agent. Chemotherapy* 36:1460–1465, have suggested that in the case of Gram(−) bacteria, permeabilization of the outer membrane followed by the depolarization of the cytoplasmic membrane is the lethal event in the bactericidal action of TP. The linear derivatives (containing Ala or chemically modified cysteines) adopt a random structure in solution, and the loss of antimicrobial activity has been attributed to the elimination of the spatial configuration of the arginine side-chains. In contrast, in this paper we demonstrate that, with the exception of TPD and TPA which are fairly inactive, the antimicrobial activity of the linear derivatives against fungi, Gram(−) and Gram(+) bacteria (Tables 2 and 3) is remarkably similar to the disulfide-linked native peptide. Unlike the bacterial cells, however, the eukaryotic fungal cell is more complex and less well characterized. Although it is reasonable to expect differences in cell wall composition and structure among different fungal species, the structure of *C. albicans* cell wall may serve a useful paradigm (Reiss et al. (1992) *J. Med. & Vet. Mycology* 30, supplement 1, 143–156). Here, the outermost layer is composed of mannoprotein containing highly charged phosphate groups that probably enables the pathogen to attract and attach to other molecules, including basic peptides. Although the mechanism of fungicidal action is unknown, it is conceivable that cationic peptides bind to negatively charged head groups and eventually make their way into the cell to disrupt the cytoplasmic membrane. Indeed, the antibiotic amphotericin B exerts its antifungal activity by physical disruption of the structural integrity of the fungal cytoplasmic membrane (Andreoli et al. (1968) *J. Gen. Physiol.* 52:300–325; Cass et al. (1970) *J. Gen. Physiol.* 56:100–124 and *Proc. Natl. Acad. Sci. USA* 85:5072–5076). In any event, it seems likely that the target of these peptides is the cell membrane and the process of membrane disruption may involve either the formation of pores through a "barrel-stave" mechanism (Wade et al. (1990) *Proc. Natl. Acad. Sci. USA* 87:4761–4765; Bessalle et al. (1990) *FEBS Lett.* 274:151–155) or the peptides bind parallel to the surface of the membrane as a "carpet" and dissolve the membrane in a detergent like manner (Pouny et al. (1992) *Biochemistry* 31:12416–12423; Gazit et al. (1995) *Biochemistry* 34:11479–11488; Sai, Y. (1995) *Trends Biochem. Sci.* 20:460–464).

On the basis of numerous other studies, the accepted and even growing opinion in the field of antimicrobial peptides is that biological activity is a function of amphipathic structure (α-helical or disulfide-linked β-sheet) and high cationic charge. However, studies such as this challenge that paradigm and suggest that amino acid substitutions can introduce subtle structural changes that have to be interpreted in the context of the overall hydrophobicity, the bulkiness of the non-polar face, the net charge, the hydrophilicy of the polar face and the lipid composition of the pathogen membrane. Indeed, structure may be less important for antimicrobial activity than envisaged. For example, based on the bioactivity of short peptides (9–10 residues) with little or no α-helicity, Bessalle et al. (1993) *J. Med. Chem.* 36:1203–1209, have argued that it maybe an over interpretation to correlate bioactivity strictly with amphiphilicity. More recently, working with synthetic diastereomeric peptides, Oren et al. (1997) *J. Biol. Chem.* 272:14643–14649, have shown that derivatives that are totally devoid of α-helical -structure, but have a high ratio of hydrophilic to hydrophobic residues, still retain the full antimicrobial activity of the parent peptide. On the other hand, preserving the structure and increasing the hydrophobicity were important parameters for mammalian cell lysis. Thus, one major design criterion for synthetic peptides with antimicrobial activity but without mammalian cell cytotoxicity must involve balancing the hydrophobicity-hydrophilicity ratio at the expense of an ordered structure.

That which is claimed is:

1. A compound of the formula SEQ ID NO:2:

$$KWX_1FRVX_2YRGIX_3YRRX_4R$$

wherein $X_1$, $X_2$, $X_3$, and $X_4$ is one amino acid selected from the group consisting of isoleucine, valine, methionine, phenylalanine, tyrosine, wherein $X_{1-4}$ are the same amino acid.

2. The compound of claim 1, wherein each of $X_1$, $X_2$, $X_3$, and $X_4$ is isoleucine.

3. The compound of claim 1, wherein each of $X_1$, $X_2$, $X_3$, and $X_4$ is valine.

4. The compound of claim 1, wherein each of $X_1$, $X_2$, $X_3$, and $X_4$ is methionine. leucine.

5. The compound of claim 1, wherein each of $X_1$, $X_2$, $X_3$, and $X_4$ is phenylalanine.

6. The compound of claim 1, wherein each of $X_1$, $X_2$, $X_3$, and $X_4$ is tyrosine.

7. A method of protecting a plant from pathogens said method comprising subjecting said plant to a pathogen-inhibiting amount of an antimicrobial compound, said compound is of the formula SEQ ID NO: 2:

$$KWX_1FRVX_2YRGIX_3YRRX_4R$$

wherein $X_1$, $X_2$, $X_3$, and $X_4$ is one amino acid selected from the group consisting of isoleucine, valine, methionine, phenylalanine, tyrosine, wherein $X_{1-4}$ are the same amino acid.

8. The method of claim 7, wherein each of $X_1$, $X_2$, $X_3$, and $X_4$ is methionine.

9. The method of claim 7, wherein each of $X_1$, $X_2$, $X_3$, and $X_4$ is isoleucine.

10. The method of claim 7, wherein each of $X_1$, $X_2$, $X_3$, and $X_4$ is valine.

11. The method of claim 7, wherein each of $X_1$, $X_2$, $X_3$, and $X_4$ is phenylalanine.

12. The method of claim 7, wherein each of $X_1$, $X_2$, $X_3$, and $X_4$ is tyrosine.

13. A transformed plant comprising within its genome a chimeric gene said gene comprising a promoter which drives expression in a plant cell operably linked to a nucleotide sequence encoding an antimicrobial peptide of the formula SEQ ID NO: 2:

$$KWX_1FRVX_2YRGTX_3YRRX_4R$$

wherein $X_1$, $X_2$, $X_3$, and X4 is one amino acid selected from the group consisting of isoleucine, valine, methionine, phenylalanine, tyrosine, where $X_{1-4}$ is the same amino acid, wherein said sequence is operably linked to a promoter which expresses in a plant cell.

14. The method of claim 13, wherein each of $X_1$, $X_2$, $X_3$, and $X_4$ is methionine.

15. The method of claim 13, wherein each of $X_1$, $X_2$, $X_3$, and $X_4$ is isoleucine.

16. The method of claim 13, wherein each of $X_1$, $X_2$, $X_3$, and $X_4$ is valine.

17. The method of claim 13, wherein each of $X_1$, $X_2$, $X_3$, and $X_4$ is phenylalanine.

18. The method of claim 13, wherein each of $X_1$, $X_2$, $X_3$, and $X_4$ is tyrosine.

19. The method of claim 13, wherein said plant is selected from the group consisting of maize, wheat, sorghum, sunflower, and soybean.

20. The plant of claim 13, wherein said plant is a monocot.

21. The plant os claim 13, wherein said plant is a dicot.

22. The plant of claim 20 wherein said monocot is maize.

23. Seed of the plant of claim 13.

24. Seed of the plant of claim 22.

* * * * *

UNITED STATES PATENT AND TRADEMARK OFFICE
CERTIFICATE OF CORRECTION

PATENT NO. : 6,015,941
DATED : January 18, 2000
INVENTOR(S) : Rao

It is certified that error appears in the above-identified patent and that said Letters Patent is hereby corrected as shown below:

Column 17, in Table 3, column 3, line 3, under the subheading "50µg zone size (mm)", "17" should read --18--.
Column 23, line 28, "SEQ ID NO:2" should read --(SEQ ID NO:2)--; line 40, cancel "leucine."; line 48, "SEQ ID NO:2" should read --(SEQ ID NO:2)--.
Column 24, line 35, "SEQ ID NO:2" should read --(SEQ ID NO:2)--; line 36, the formula "$KWX_1FRVX_2YRGTX_3YRRX_4R$" should read --$KWX_1FRVX_2YRGIX_3YRRX_4R$--; line 37, "X4" should read --$X_4$--; line 57, "os" should read --of--.

Signed and Sealed this

Fifth Day of December, 2000

*Attest:*

Q. TODD DICKINSON

*Attesting Officer*       *Director of Patents and Trademarks*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 17 amino acids
      (B) TYPE: amino acid
      (C) STRANDEDNESS: single
      (D) TOPOLOGY: linear -continued

```
    (ii) MOLECULE TYPE: peptide (xi) SEQUENCE DESCRIPTION: SEQ ID NO:1:

Lys Trp Cys Phe Arg Val Cys Tyr Arg Gly Ile Cys Tyr Arg Arg Cys
1               5                   10                  15

Arg (2) INFORMATION FOR SEQ ID NO:2:

(i) SEQUENCE CHARACTERISTICS:
         (A) LENGTH: 17 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:2:

Lys Trp Xaa Phe Arg Val Xaa Tyr Arg Gly Ile Xaa Tyr Arg Arg Xaa
1               5                   10                  15

Arg
```